US006967106B2

(12) United States Patent
Simon

(10) Patent No.: US 6,967,106 B2
(45) Date of Patent: Nov. 22, 2005

(54) HUMAN MEDICAL TREATMENT BY AEROSOL INHALATION OF IMMUNOGLOBULIN A

(76) Inventor: Michael R. Simon, 1925 Scottwood, Ann Arbor, MI (US) 48104

( * ) Notice: Subject to any disclaimer, the term of this patent is extended or adjusted under 35 U.S.C. 154(b) by 394 days.

(21) Appl. No.: 10/246,158

(22) Filed: Sep. 18, 2002

(65) Prior Publication Data

US 2003/0021778 A1    Jan. 30, 2003

Related U.S. Application Data

(63) Continuation-in-part of application No. 09/815,026, filed on Mar. 22, 2001, now Pat. No. 6,932,967.

(51) Int. Cl.$^7$ ............... G01N 33/563; G01N 33/536; A61K 39/395; A61K 39/00; C12P 21/08
(52) U.S. Cl. ................. 436/513; 436/547; 424/130.1; 424/178.1; 435/69.1
(58) Field of Search .................. 436/513, 547; 424/134.1, 141.1, 178.1, 130.1, 178; 435/69.1

(56) References Cited

U.S. PATENT DOCUMENTS

| 5,258,177 A | 11/1993 | Uemura et al. |
| 5,670,626 A | 9/1997 | Chang |
| 5,808,000 A | 9/1998 | Mannhalter et al. |
| 6,019,968 A | 2/2000 | Platz et al. |
| 6,063,905 A | 5/2000 | Capra et al. |
| 6,124,132 A | 9/2000 | Blake |

FOREIGN PATENT DOCUMENTS

| DE | 4 122 784 | 1/1993 |
| EP | 1 068 871 A1 | 1/2001 |

OTHER PUBLICATIONS

Murkofsky et al, J Biol Chem 254(23): 12181-12184, 1979.*
Michetti et al, Adv Exp Med Biol 310: 183-5, 1991.*
Zikan et al, Mol Immunol 23(5): 541-4, May 1986.*
Bezares et al. "Prevencion de infecctiones en pacientes con sindromes linfoproliferativos y mieloma por nebulizacion de un concentrado de IgA" Sangre 1997; 42(3):219-222.
Sanchez Avalos et al. "Nebulizaciones con IgA humana en pacientes con hipogammaglobulinemia e infecciones de las vias aereas secundararias a enfermedades linfoproliferativas" Medicina (Buenos Aires) 1995: 55(6): 727-729.
Leibel et al. "Method for the isolation of biologically active monomeric immunoglobulin A from a plasma fraction" Journal of Chromatography B, 678 (1996) 173-180.
Document bibliography and abstract, Patent WO 0103727.
Document bibliography and abstract, Patent CS242310.
Berzofsky et al. "Monoclonal Antibodies in Chapter 12, Antigen-Antibody Interactions and Monoclonal Antibodies"
pp. 455-465 in Fundamental Immunology, Third Edition, W.E. Paul (ed.), Raven Press, NY 1993.
Cohn et al. "Preparation and Properties of Serum and Plasma Proteins IV. A System for the Separation into Fractions of the Protein and Lipoprotein Components of Biological Tissues and Fluids" J. Am. Chem. Soc. 1946, 68:459-475.
Corthesy, "Recombinent Secretory IgA for Immune Intervention Against Mucosal Pathogens" Biochem. Soc. Trans. 1997, 25:471-475.
Crottet et al. "Expression, Purification and Biochemical Characterization of Recombinant Murine Secretory Component, A Novel Tool in Mucosal Immunology" Biochem. J. 1999, 341:299-306.
Fahy et al. "Effect of Aerosolized Anti-IgE (E25) on Airway Responses to Inhaled Allergen in Asthmatic Subjects" Am. J. Respir. Crit. Care Med. 1999, 160:1023-1027.
Fruchtman et al. "Aerosol Administration of Human Gamma Globulin as Prophylaxis Against Influenza Virus Challenge" Clin. Med. 1972 (Sep.), 79:17-20.
Giraudi et al. "Upper Respiratory Infections in Children. Response to Endonasal Administration of IgA" Int. J. Pediatr. Otorhinolaryngol. 1997, 39:103-110.
Heikkinen et al. "Intranasally Administered Immunoglobulin for the Prevention of Rhinitis in Children" Pediatr. Infec. Dis. J. 1998, 17:367-372.
Hemmingsson et al. "Nasal Administration of Immunoglobulin as Effective Prophylaxis Against Infections in Elite Cross-Country Skiers" Scand. J. Infect. Dis. 1993, 25:73-75.
Johansen et al. "Recombinant expression of polymeric IgA: incorporation of J chain and secretory component of human origin" Eur. J. Immunol. 1999, 29:1701-1708.
Kohler et al. "Continuous Cultures of Fused Cells Secreting Antibody of Predetermined Specificity" Nature 1975, 256: 495-497.

(Continued)

*Primary Examiner*—Christina Chan
*Assistant Examiner*—Phoung Huynh
(74) *Attorney, Agent, or Firm*—Gifford, Krass, Groh, Sprinkle, Anderson & Citkowski, P.C.

(57) ABSTRACT

Pooled human plasma is processed by cold ethanol fractionation to produce purified immunoglobulin G antibodies for intravenous administration. Immunoglobulin A is an unwanted by-product since intravenous administration of immunoglobulin A-containing immunoglobulin G can cause life-threatening anaphylaxis in some people. The present invention is the topical application of immunoglobulin A coupled with J chain, and optionally coupled with secretory component in order to render the immunoglobulin A more physiologically active, for the prevention or treatment of ocular diseases including ocular immune deficiency and infections. Antigen-specific monoclonal immunoglobulin A may be used.

9 Claims, No Drawings

OTHER PUBLICATIONS

Lindberg et al. "Effect of Treatment with Nasal IgA on the Incidence of Infectious Disease in World-Class Canoeists" Int. J. Sports Med. 1996, 17:235-238.

Lullau et al. "Antigen Binding Properties of Purified Immunoglobulin A Antibodies" J. Biol. Chem. 1996, 271: 16300-16309.

Mazanec et al. "Comparison of IgA versus IgG Monoclonal Antibodies for Passive Immunization of the Murine Respiratory Tract" Virus Res. 1992, 23:1-12.

Mazanec et al. "Immunoglobulin A Monoclonal Antibodies Protect Against Sendai Virus" J. Virol. 1987, 61:2624-2626.

Oncley et al. "The Separation of the Antibodies, Isoagglutinins, Prothrombin, Plasminogen and B1-Lipoprotein into Subfractions of Human Plasma" J. Am. Chem. Soc. 1949, 71:541-550.

Outlaw et al. "Mechanisms of Neutralization of Influenza Virus on Mouse Tracheal Epithelial Cells by Mouse Monoclonal Polymeric IgA and Polyclonal IgM Directed Against the Viral Haemaglutinen" J. Gen. Virol. 1990, 71:69-76.

Rimensberger et al. "Clinical Experience with Aerosolized Immunoglobulin Treatment of Respiratory Syncytial Virus Infection in Infants" Pediatr. Infect. Dis. J. 1994, 13:328-330.

Rindisbacher et al. "Production of Human Secretory Component with Dimeric IgA Binding Capacity Using Viral Expression Systems" J. Biol. Chem. 1995, 270:14220-14228.

Strong et al. "Blood Fractionation" pp. 576-602 in Vol. 3, Kirk-Othmer Encyclopedia of Chemical Technology. Second Edition, H.F. Mark et al. (eds.), Interscience Publishers, NY 1963.

Symersky et al. "Expression of the Recombinant Human Immunoglobulin J Chain in *Escheria coli*" Mol. Immunol. 2000, 37:133-140.

Tamara et al. "Cross-Protection Against Influenza A Virus Infection by Passively Transferred Respiratory Tract IgA Antibodies to Different Haemagglutinen Molecules" Eur. J. Immunol. 1991, 21:1337-1344.

Tamura et al. "Functional Role of Respiratory Tract Haemagglutinen-Specific IgA Antibodies in Protection Against Influenza" Vaccine 1990, 8:479-485.

Taylor et al. "Mechanism of Neutralization of Influenza Virus by Secretory IgA is Different from that of Monomeric IgA or IgG" J. Exp. Med. 1985, 161:198-209.

Weltzin et al. "Intranasal Monoclonal Immunoglobulin A Against Respiratory Syncytial Virus Protects Against Upper and Lower Respiratory Tract Infections in Mice" Antimicrob. Agents Chemother. 1994, 38:2785-2791.

Weltzin et al. "Intranasal Monoclonal IgA Antibody Against Respiratory Syncytial Virus Protects Rhesus Monkeys Against Upper and Lower Respiratory Tract Infection" J. Infect. Dis. 1996, 174:256-261.

Wolff et al. "Generation of Aerosolized Drugs" J. Aerosol Med. 1994, 7:89-106.

* cited by examiner

HUMAN MEDICAL TREATMENT BY AEROSOL INHALATION OF IMMUNOGLOBULIN A

RELATED APPLICATION

This application is a continuation-in-part of U.S. patent application Ser. No. 09/815,026 filed Mar. 22, 2001 now U.S. Pat. No. 6,932,967.

FIELD OF THE INVENTION

The present invention relates to human medical treatment using immunoglobulin A (IgA). More specifically the invention relates to treatment of immunodeficiencies and viral or bacterial infections by administering doses of a composition rich in immunoglobulin A to the surface of the eye.

BACKGROUND OF THE INVENTION

Immunoglobulins (also called antibodies) are a group of structurally related proteins composed of heavy and light chains. These proteins are categorized as IgM, IgG, IgD, IgE, and IgA depending upon the characteristics of the constant regions of their heavy chains (designated $\mu$, $\gamma$, $\delta$, $\epsilon$, and $\alpha$, respectively). The variable regions of the heavy chains along with the variable regions of the light chains determine the molecular (antibody) specificity of the complete molecule. These molecules are secreted by B lymphocytes in response to signals from other components of the immune system. Their function is to prevent and combat infection by viruses and bacteria.

Purified IgG from pooled human plasma is administered intravenously in humans to treat a variety of conditions. In the purification, a fraction rich in IgA is considered an unwanted by-product, since intravenous administration of IgA-containing immunoglobulin G can cause life threatening anaphylaxis in some patients.

IgA on mucosa is produced locally and not derived from circulating IgA. IgA is one of the $\gamma$ globulins on the basis of its electrophoretic mobility. IgA is composed of two $\alpha$ heavy chains and two light chains. It may be monomeric (i.e. a single molecule), dimeric (composed of two molecules) or trimeric (composed of three molecules). IgA monomers are joined together as dimers at the constant regions of their heavy chains by a J chain. IgA is secreted as one of two subclasses, IgA1 and IgA2. IgA1 predominates in the circulating blood wherein most of it occurs as a monomer. Most IgA on mucosal surfaces, such as the surfaces of the trachea, bronchi, and bronchioles in the lungs, occurs as dimers or trimers joined by J chains. IgA dimers and trimers have an increased ability to bind to and agglutinate target molecules (antigens). Agglutinated antigens are more readily phagocytosed and thereby eliminated. In addition, IgA dimers and trimers, because of the presence of their J chains, have the ability to attach to secretory component. Such molecules then have increased resistance to proteolytic enzymatic degradation. Human J chains (Symerski et al., Mol Immunol 2000; 37:133–140) and murine secretory component (Crottet et al., Biochem J 1999; 341:299–306) have been produced by genetic recombinant biological techniques. Recombinant expression of polymeric IgA with the incorporation of J chain and secretory component of human origin has been accomplished (Johansen et al., Eur J Immunol 1999; 29:1701–1708). Recombinant expression of antigen-specific monoclonal IgA bound to J chain within hybridoma cells before secretion has also been accomplished (Sun et al., Biotechnology 1995; 13:779–786 and U.S. Pat. No. 5,670,626 to Tse Wen Chang entitled "Allergen-Specific Human IgA Monoclonal Antibodies for Mucosal Administration").

IgA can attach to the cell surface of phagocytic leukocytes and thereby facilitate antibody-dependent cell-mediated killing of microorganisms. It also interacts with lactoperoxidase and lactoferrin which enhances the latter's antibacterial actions. Monomeric IgA interferes with influenza virus replication (Taylor et al., J Exp Med 1985;161:198–209) and polymeric IgA interferes with influenza binding to and entry into target cells (Taylor et al., J Exp Med 1985;161:198–209; Outlaw and Dimmock, J Gen Virol 1990;71:69–76).

Tear secretory IgA enhances neutrophil chemotaxis (Lan JX et al., Aust N Z J Ophthalmol 1998;26 Suppl 1:S36–39). It inhibits Pseudomonas binding to the cornea and protects mice against bacterial keratitis (Masinick et al., Invest Ophthalmol Vis Sci 1997;38:910–918). Natural and monoclonal anti-Acanthoameba secretory IgA in tears inhibits Acanthoameba infection in hamsters by similarly decreasing binding of the protozan to the cornea. (Leher HF et al., Invest Ophthalmol Vis Sci 1998:39:2666–2773, Leher H et al., Exp Eye Res 1999; 69:75–84). Ocular secretory IgA also protects against ocular infection and establishment of latency by herpes simplex virus type 1 in mice (Richards C M et al., J Infect Dis 1998;177:1451–1457) and rabbits (Nesburn A B et al., Virol 1998; 252:200–209). Topically applied IgA (250 ug/ml) derived from milk inhibits binding of Pseudomonas to mouse cornea (Masinick et al., Invest Ophthalmol Vis Sci 1997;38:910–918).

Exogenous IgA has been topically applied to the nose in both animals and humans for the purpose of preventing and treating disease. In mice, nasal application of exogenous IgA has been demonstrated to be efficacious in protecting animals from influenza (Tamura et al., Vaccine 1990;8:479–485, Tamura et al., Eur J Immunol 1991;21:1337–1344), Sendai virus (Mazanec et al., J Virol 1987;61:2624–2626, Mazanec et al., Virus Res 1992;23:1–12) and respiratory syncytial virus (Weltzin et al., Antimicrob Agents Chemother 1994;38;2785–2791) challenge. Intranasal monoclonal IgA also protects rhesus monkeys against respiratory syncytial virus infection (Weltzin et al., J Infect Dis 1996;174:256–261). In humans, nasal administration of approximately 70% IgA/30% IgG resulted in decreased frequency of upper respiratory tract infections in elite skiers (Hemmingsson and Hammarstrom, Scand J Infect Dis 1993; 25:73–75), and in children (Giraudi et al., Int J Pediatr Otorhinolarynol 1997;39:103–110, Heikkinen et al., Pediatr Infect Dis J 1998;17:367–372) but not in elite canoeists (Lindberg and Berglund, Int J Sports Med 1996;17:2335–238).

Aerosol administration of human $\gamma$ globulin (Fruchtman et al., Clin Med 1972 (Sept);79:17–20), pooled human IgG (Rimensberger and Schaad, Pediatr Infect Dis J 1994;13:328–330) and murine recombinant humanized IgG (Fahy et al., Am J Respir Crit Care Med 1999;160:1023–1027) has demonstrated that there are no adverse effects from the aerosol inhalation of human $\gamma$ globulin or human or humanized IgG. Topical administration of serum containing IgA to the surface of the eye has similarly demonstrated that there are no adverse effects from such applications (Fox et al., Arthritis Rheum 1984; 27:459–461, Tsubota K et al., Am J Ophthalmol 1996;122:38–52, Tsubota K et al., Ophthalmol 1999;106:1984–1989, Tsubota K et al., Br J Ophthalmol 1999;83:390–395).

Individuals suffering from hypogammaglobulinemia or with a local deficiency of IgA production such as that due to lack of tears, have been treated by a number of means, none of which has proven to be completely satisfactory. On the one hand, such patients have been treated by administration of antibiotics, either topical or local. However, antibiotic treatment is not completely effective in preventing infection in patients with immunoglobulin deficiency or whose immune systems are otherwise compromised. For example, infectious conjunctivitis is found in patients with lack of local immunoglobulin production.

Another method of treating such patients has been intravenous infusion of immunoglobulin. The immunoglobulin administered by intravenous infusion does not contain the secretory piece. As a result, the infused immunoglobulin may not reach the mucosal surface of a mucous membrane as found in the bronchial tree or eye. In addition, intravenous infusion of immunoglobulin is usually administered by trained medical personnel and can be associated with systemic reactions. There is thus a need for methods which can be used to deliver IgA to mucosal surfaces such as the bronchial mucosal and ocular conjunctival surfaces. It would be advantageous if such treatment could be administered by the patient without the need for intervention by trained medical personnel. It would further be desirable to make use of unwanted by-products resulting from the preparation of purified immunoglobulin G from pooled human plasma. The present invention provides these advantages and others as will be apparent to one with skill in the art from the disclosure that follows.

SUMMARY OF THE INVENTION

The invention provides a method for medical treatment of humans that involves pulmonary administration by inhalation and topical application of an immunoglobulin (Ig) A composition. Topical application of an IgA composition may be made to any local area such as to the surface of the eye. In one embodiment, the IgA is prepared as a by-product from pooled human plasma and is derived from a Cohn fraction component enriched in IgA. In another embodiment, the IgA composition contains a monoclonal antigen-specific IgA. In a preferred embodiment, the IgA component is further combined with recombinant human J chains and recombinant secretory component to produce a more physiologically effective composition. In another embodiment, the IgA composition contains a monoclonal antigen-specific IgA which is further combined with recombinant human J chains and recombinant secretory component after the production and secretion of the monoclonal IgA. Conditions treatable by pulmonary or topical administration of such compositions include immunodeficiency diseases, immune suppression, bacterial infections, and viral infections.

DETAILED DESCRIPTION OF THE PREFERRED EMBODIMENTS

The following description of the preferred embodiment(s) is merely exemplary in nature and is in no way intended to limit the invention, its application, or uses.

In one embodiment, the invention provides a method for medical treatment of humans comprising the step of administering by inhalation an aerosol composition. In another embodiment, administration of the composition is by topical application. The aerosol or topical composition contains an IgA component which can be derived from a number of sources. A preferred source of IgA is obtained from a by-product of human plasma processing in preparation of commercially available isolated plasma components. The by-product is obtained from pooled human plasma following Cohn cold ethanol fractionation to produce fraction III precipitate as performed by those of skill in the art of protein separation. IgA by-product is further purified by adsorption onto a ion exchange medium in neutral or slightly acidic conditions as performed by those of skill in the art of protein purification.

A more detailed description of isolation of an IgA component as a by-product from pooled human plasma or hyperimmune pooled human plasma is as follows. Ethanol fractionation of pooled human plasma is a well known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. This is because some individuals undergo an anaphylactic-like reaction if treated with intravenous IgG that contains IgA as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted by-product. The IgA by-product is further purified by heparin-Sepharose adsorption, dextran sulfate and ammonium sulfate precipitation, hydroxyapatite chromatography, batch adsorption by an anion-exchange matrix and gel permeation as performed by those of skill in the art of protein purification (Leibl H et al., J Chromatogr B Biomed Appl 1996;678:173–180 and U.S. Pat. No. 5,808,000) the disclosure of which is expressly incorporated herein by reference. An alternative purification method is disclosed in U.S. Pat. No. 5,258,177, the disclosure of which is expressly incorporated herein by reference. According to the invention, this unwanted IgA following ion exchange adsorption purification and other steps in the isolation procedure is further treated by incubation with immobilized hydrolases to inactivate viruses and vasoactive substances. Such treatment has been proven to eliminate many viruses tested including HIV, Sindbis, and vaccinia. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., J Am Chem Soc 1946;68:459–475, Oncley et al., J Am Chem Soc 1949;71:541–550, and in most detail in pages 576–602, Kirk-Othmer Encyclopedia of Chemical Technology, Vol 3, second edition (1963), the disclosure of which is hereby expressly incorporated by reference.

In a preferred embodiment, the compositions of the invention contain, in addition to the IgA component, one or more further components selected from the group consisting of recombinant human J chains, recombinant secretory component, and combinations thereof. The production of human J chains by genetically recombinant biological techniques is disclosed in Symerski et al., Mol Immunol 2000; 37:133–140, the disclosure of which is hereby incorporated by reference. Human secretory component can be produced by recombinant techniques as described in Rindisbacher et al., J Biol Chem 1995; 23:14220–14228, disclosure of which is hereby incorporated by reference. Recombinant J chains and secretory component from non-human species are produced for compositions to be used in non-human species as described in Kulseth and Rogne DNA Cell Biol 1994 January; 13(1):37–42; Takahashi et al., Immunogenetics. 2000 February; 51(2):85–91; and Crottet et al., Biochem J 1999; 341:299–306. In a preferred embodiment the IgA may be coupled to recombinant J chains by disulfide bonding which is accomplished in mildly oxidizing conditions. The resulting IgA-J chain conjugates are purified. IgA-J chain conjugates may then be further coupled to recombinant secretory component. In a preferred embodiment, the coupling is accomplished by forming disulfide bonds under mildly oxidizing conditions. IgA containing both J chain and secretory component is again purified by ion-exchange and size exclusion chromatography and/or ultrafiltration as described in Lullau et al., J. Biol Chem 1996; 271:16300–16309, Corthesy, Biochem Soc Trans 1997; 25:471–475, and Crottet et al., Biochem J 1999; 341: 299–306, as performed by those of skill in the art of protein purification, the disclosures of which are hereby incorporated by reference. While recombinant expression of IgA with the incorporation of J chain and secretory component has been accomplished, hybridoma production of IgA may not include incorporated J chains and secretory component. According to the invention, the recombinant J chains, recombinant secretory component, or mixtures of them may be combined with the monoclonal IgA after production of the IgA by hybridoma techniques. Such IgA may be coupled to recombinant J chains and secretory component as described above. Purified IgA containing J chain and secretory components can be stabilized for example by the addition of human serum albumin to a final concentration of 5%. The presence of the human J chains and secretory component in the compositions of the invention leads to inhaled or topically applied doses of immunoglobulin which are more physiologically effective than compositions without such components.

In another embodiment, an IgA containing component is isolated as a by-product from hyperimmune pooled human plasma for coupling with J chain and secretory component. Hyperimmune pooled human plasma is obtained from multiple donors who have been immunized against a specific disease. In this method, donors are exposed to a chosen antigen according to a protocol which is defined according to the desired result as illustrated in U.S. Pat. No. 6,054,127 which is hereby incorporated by reference.

In another embodiment, the IgA component can be prepared by hybridoma techniques to provide antigen-specific IgA. Hybridoma techniques are described originally in Kohler and Milstein, Nature 1975;256:495–497 with more recent advances summarized in Berzofsky et al., Fundamental Immunology, Third Edition, 1993, pp 455–462, the disclosures of which are hereby incorporated by reference. Hybridoma production involves the fusion of an immortalized immunoglobulin-producing myeloma cell with an antibody-producing cell from an immunized individual. The product is an immortalized cell culture which produces the specific antibody against the antigen that the donor individual is immune to. For example, a mouse monoclonal IgA antibody has been prepared against respiratory syncytial virus F glycoprotein as described in Weltzin et al., J Infect Dis 1996;174:256–261 and Weltzin et al., Antimicrob Agents Chemother 1994;38:2785–2791. Hybridoma technology includes techniques for making chimeric and humanized monoclonal antibodies, for example, as described in H. Zola, Monoclonal Antibodies: Preparation and Use of Monoclonal Antibodies and Engineered Antibody Derivatives, 1999, Springer-Verlag and U.S. Pat. No. 6,235,883, both of which are incorporated herein by reference.

The compositions of the invention for aerosol delivery and topical delivery generally contain in addition to the IgA component and optional J chains and secretory component, known pharmaceutical excipients and buffering agents. Non-limiting examples of such excipients include proteins as for example, human serum albumin and recombinant human albumin. In general, for topical application, a composition contains pharmaceutical excipients and buffering agents ranging from 1% to 99% of the total weight of the composition. Other pharmaceutical excipients include carbohydrates, sugars, and alditols. Non-limiting examples of suitable carbohydrates include sucrose, lactose, raffinose, and trehalose. Suitable alditols include mannitol, and pyranosyl sorbitol. Polymeric excipients include polyvinylpyrrolidone, Ficolls, soluble hydroxyethyl starch, and the like of suitable molecular weight. Non-limiting examples of suitable buffering agents include salts prepared from organic acids such as citric acid, glycine, tartaric acid, lactic acid, and the like. Other useful excipients include surfactants and chelating agents.

The compositions of the invention are readily aerosolized and rapidly deposited in the lungs of a host. Doses are formulated from the compositions of the invention by combining the IgA component with or without human J chain and secretory component, and pharmaceutical excipients so as to contain an effective dose of the active ingredient. A typical dose for pulmonary administration would include about 5 milligrams of active material. The pulmonary dose amount may be adjusted up or down as required to meet the treatment needs of a subject, or to provide for ease and convenience in administering the dose.

The compositions of the invention are readily formulated for delivery to a subject by topical application. Appropriate target areas for topical application depend on the goal of the preventative or therapeutic treatment and are readily determined by one skilled in the art and commonly include sites where local action is desirable. Generally such target areas illustratively include the mouth, gastrointestinal tract, genitourinary tract, nose, sinuses, ear and eye and in particular the mucosal surfaces of those areas. A target area as described above is further composed of target sub-areas which are treated separately from the whole target area. For example, a composition of the invention is instilled into the bladder, thus treating a sub-area of the genitourinary tract target area. Examples of other sub-areas illustratively include stomach, small intestine, large intestine, colon, rectum, vaginal cavity, external genitalia, kidney and urethra. Further sites appropriate for topical application illustratively include targeted areas of the skin or body susceptible to infection, such as a wound, or an area of pathology due to immune deficiency, such as a lesion. Topical application as used herein does not include application to certain target areas such as the respiratory mucosa.

A particular inventive composition is more appropriate for topical application to a selected target area than another embodiment of the invention. For example, for nasal application, IgA in combination with recombinant J-chain or recombinant secretory component or both is administered. However, topical application of isolated IgA alone to nasal mucosa is not an embodiment of the present invention.

Formulations of IgA for topical application include concentrations ranging from 1 mg/ml to 600 mg/ml. In an embodiment of the present invention, a single topically applied dose of IgA ranges from 0.1 mg per cm$^2$ of target area to 600 mg per cm$^2$ of target area. In a more preferred embodiment of the present invention, the topically applied dose of IgA ranges from 1 mg per cm$^2$ of target area to 60 mg per cm$^2$ of target area. In a still more preferred embodiment of the present invention, the topically applied dose of IgA ranges from 2 mg per cm$^2$ of target area to 25 mg per cm$^2$ of target area. The single topical dose amount may be adjusted up or down as required to meet the treatment needs of an individual, or to provide for ease and convenience in administering the dose. The number of doses to be administered per day depends on the condition to be treated as well as the target area to which the composition is topically administered. In general the number of doses per day ranges from 1–12, preferably ranging from 1–4. The exact amount of the antibody or therapeutic agent required will vary from subject to subject, depending on the age, weight and general condition of the subject, the severity of the disease that is being treated, the particular compounds used, the mode of administration, and the like. An appropriate amount may be determined by one of ordinary skill in the art using only routine experimentation given the teachings herein.

The compositions will include an effective amount of the selected agent in combination with a pharmaceutically acceptable carrier and, in addition, may include other medicinal agents, pharmaceutical agents, carriers, or diluents. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

An illustrative example of a pharmaceutically acceptable formulation of the IgA composition of the present invention is an electrolyte solution containing 129 mEq/l Na$^+$, 17 mEq/l K$^+$, 0.32 mEq/l Ca$^{++}$, 0.35 mEq/l Mg$^{++}$, 0.11 mEq/l Zn$^{++}$, 141 mEq/l Cl$^-$ and 12 mEq/l bicarbonate, pH 7.7.

Compositions suitable for topical, pulmonary or other route of administration may comprise physiologically acceptable sterile aqueous or nonaqueous solutions, dispersions, suspensions or emulsions, and sterile powders for reconstitution into sterile solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. These compositions may also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and solutions. The active component is admixed under sterile conditions with a physiologically acceptable carrier and any preservatives, buffers, or propellants as may be required. Ophthalmic formulations, eye ointments, powders, and solutions are specifically contemplated as being within the scope of this invention.

Pharmaceutically acceptable salts, esters and amides of components of the compositions of the present invention are used. The term "pharmaceutically acceptable salts, esters and amides" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like.

These may include cations based on the alkalai and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge et al., "Pharmaceutical Salts," J. Pharm. Sci., 1977; 66:1–19 which is incorporated herein by reference.)

The compositions of the invention can be administered by nebulization or by metered dose inhalers. Nebulizers and metered dose inhalers are well known in the art and are described for example, in Wolff and Niven, J Aerosol Med 1994;7:89–106.

Compositions of the present invention are added to other topical ophthalmological preparations. Non-limiting examples of these are Bion Tears, Tears Natural II, Tears Natural Free, all Alcon, Canada; Theratears, Advanced Vision Research; Refresh Tears, Liquifilm Tears, Refresh Plus, and Tears Plus Lubricant, all Allergan Pharmaceuticals; Murocel, Bausch and Lomb Pharmaceuticals; Genteal Lubricating Eye Drops, CIBA Vision; Ocutears PF and Ocu-Tears, Ocumed; Lubrifair Solution and Tearfair Solution, Pharmafair.

Diseases and conditions for which aerosol pulmonary administration of the compositions of the invention is to be used therapeutically or prophylactically include, but are not limited to: common variable immunodeficiency, IgA deficiency, human immunodeficiency virus (HIV) infection, lower respiratory tract infection with influenza, lower respiratory tract infection with respiratory syncytial virus, lower respiratory tract infection with rhinovirus, lower respiratory tract infection with adenovirus, chronic lymphocytic leukemia, multiple myeloma, macroglobulinemia, chronic bronchitis, bronchiectasis, asthma, immune suppression associated with bone marrow transplantation, immune suppression associated with cyclophosphamide administration, immune suppression associated with azathiaprine administration, immune suppression associated with methotrexate administration, immune suppression associated with chlorambucil administration, immune suppression associated with nitrogen mustard administration, immune suppression associated with 6-mercaptopurine administration, immune suppression associated with thioguanine administration, severe combined immunodeficiency, adenosine deaminase deficiency, major histocompatibility class I (Bare leukocyte syndrome) and class II deficiencies, purine nucleoside phosphorylase deficiency, DiGeorge Syndrome, transient hypogammaglobulinemia of infancy, X-linked agammaglobulinemia, X-linked agammaglobulinemia with growth hormone deficiency, transcobalamin II deficiency, immunodeficiency with thymoma, immunodeficiency with hereditary defective response to Epstein Barr virus, immunoglobulin deficiency with increased IgM, P chain deficiency, ataxia telangiectasia, and immunodeficiency with partial albinism.

Diseases and conditions for which topical administration of the compositions of the invention is to be used therapeutically or prophylactically include, but are not limited to: bacterial and viral infections, protozoan infections such as giadiasis, yeast infections, chronic lymphocytic leukemia, multiple myeloma, macroglobulinemia, immune suppression associated with bone marrow transplantation, immune suppression associated with cyclophosphamide administration, immune suppression associated with azathiaprine administration, immune suppression associated with methotrexate administration, immune suppression associated with chlorambucil administration, immune suppression associated with nitrogen mustard administration, immune suppression associated with 6-mercaptopurine administration, immune suppression associated with thioguanine administration, severe combined immunodeficiency, adenosine deaminase deficiency, major histocompatibility class I (Bare leukocyte syndrome) and class II deficiencies, purine nucleoside phosphorylase deficiency, DiGeorge Syndrome, transient hypogammaglobulinemia of infancy, X-linked agammaglobulinemia, X-linked agammaglobulinemia with growth hormone deficiency, transcobalamin II deficiency, immunodeficiency with thymoma, immunodeficiency with hereditary defective response to Epstein Barr virus, immunoglobulin deficiency with increased IgM, P chain deficiency, ataxia telangiectasia, and immunodeficiency with partial albinism and sequelae of selective IgA deficiency such as those due to rheumatoid arthritis, juvenile rheumatoid arthritis, systemic lupus erythematosus, thyroiditis, pernicious anemia, dermatomyositis, Coomb's positive hemolytic anemia, idiopathic Addison's disease, cerebral vasculitis and idiopathic thrombocytopenic purpura.

A particular inventive composition is more appropriate for topical application to treat a particular pathology than another embodiment of the invention. For example, for treatment of immunodeficiency due to HIV infection, IgA in combination with recombinant J-chain is administered. However, topical application of secretory IgA immunoreactive with human immunodeficiency virus is not an embodiment of the present invention. In another example, where treating allergy, IgA alone or in combination with recombinant J-chain and/or recombinant secretory component is topically administered. However, topical application of allergen-specific monoclonal IgA antibodies without recombinant J-chain and/or recombinant secretory component which has been subsequently added is not an embodiment of the present invention.

Diseases and conditions for which topical ocular administration of the compositions of the invention is to be used therapeutically or prophylactically include, but are not limited to: bacterial and viral ocular infections, dry eye syndromes, post surgical and other corneal epithelial deficits, Sjogren's syndrome, tear IgA deficiency of atopic dermatitis, atopic keratoconjunctivitis, vernal conjunctivitis and allergic conjunctivitis.

As used here, the term therapeutic treatment means that the patient being administered a dose of a composition of the invention has been diagnosed as having the condition to be treated. Prophylactic treatment means that the patient is being treated to prevent infection. Such treatment is often indicated where a patient is at risk for lower respiratory tract infection or for ocular infection.

As used herein, the term subject is intended to be used interchangeably with the term patient and indicates an individual to be treated with the compositions and methods of the present invention. A subject treated with the compositions and methods of the present invention illustratively includes humans, cows, horses, pigs, goats, sheep and chicken.

EXAMPLE 1

Polyclonal IgA is obtained from pooled human plasma following Cohn cold ethanol fractionation to produce fraction III precipitate. IgA is further purified by adsorption onto an ion exchange medium in neutral or slightly acidic conditions. Alternatively, monoclonal IgA is obtained from an IgA-producing hybridoma. The IgA is then coupled to recombinant J chains by disulfide bonding which is accomplished in mildly oxidizing conditions. The molar ratio of IgA to J chain is 2:1 or 3:1. IgA-J chain conjugates are purified. IgA-J chain conjugates may then be further coupled to recombinant secretory component again by disulfide bonding in mildly oxidizing conditions, preferably at a molar ratio of secretory component to IgA-J chain conjugates of 1:1. IgA containing both J chain and secretory component is again purified. Purified IgA containing J chain and secretory component is stabilized by the addition of human serum albumin to a final concentration of 5%. The final solution, adjusted to a therapeutic dose of 5 mg IgA, is then placed in a nebulizer for self-administration.

EXAMPLE 2

Polyclonal IgA is obtained from pooled human plasma following Cohn cold ethanol fractionation to produce fraction III precipitate. IgA is further purified by heparin-Sepharose adsorption, dextran sulfate and ammonium sulfate precipitation, hydroxyapatite chromatography, batch adsorption and by an anion-exchange matrix and gel permeation. Alternatively, monoclonal IgA is obtained from an IgA-producing hybridoma. The IgA is then coupled to recombinant J chains by disulfide bonding which is accomplished in mildly oxidizing conditions. The molar ratio of IgA to J chain is 2:1 or 3:1. IgA-J chain conjugates are purified. IgA-J chain conjugates may then be further coupled to recombinant secretory component again by disulfide bonding in mildly oxidizing conditions, preferably at a molar ratio of secretory component to IgA-J chain conjugates of 1:1. IgA containing both J chain and secretory component is again purified. Purified IgA containing J chain and secretory component is stabilized by the addition of human serum albumin to a final concentration of 5%. The final solution, adjusted to a therapeutic concentration of 20 mg/ml IgA in electrolyte solution containing 129 mEq/l $Na^+$, 17 mEq/l $K^+$, 0.32 mEq/l $Ca^{++}$, 0.35 mEq/l $Mg^{++}$, 0.11 mEq/l $Zn^{++}$, 141 mEq/l $Cl^-$ and 12 mEq/l bicarbonate, pH=7.7, is then self-administered with an eyedropper.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for producing a therapeutic composition comprising the step of: combining polyclonal monomeric IgA with a recombinant J chain and a recombinant secretory component in a molar ratio of the IgA to the J chain of 2:1 and a molar ratio of an IgA-J chain conjugate to the secretory component of 1:1, wherein the recombinant J chain and secretory components are sequentially combined with the polyclonal monomeric IgA, and wherein the polyclonal monomeric IgA comprises a by-product of cold ethanol fractionation of pooled plasma derived from more than one human individual, wherein the by-product is prepared by:

- providing pooled human plasma;
- fractionating the pooled human plasma to produce a polyclonal monomeric IgA rich fraction;
- adsorbing the polyclonal monomeric IgA rich fraction onto an ion exchange medium to form a bound portion of the polyclonal monomeric IgA;
- recovering the bound portion of the polyclonal monomeric IgA;
- subjecting the recovered bound portion of the polyclonal monomeric IgA to antiviral treatment; and
- sterilizing the resulting product.

2. The method according to claim 1, wherein the pooled human plasma is derived from specifically immunized donors.

3. A method for producing a therapeutic composition comprising the step of: combining monoclonal monomeric IgA, a recombinant J chain, a recombinant secretory component, wherein the J chain and secretory components are sequentially combined with the monoclonal monomeric IgA after production of the monoclonal monomeric IgA by hybridoma techniques.

4. The method of claim 3 wherein the recombinant J chain is humanized.

5. The method of claim 3 wherein the IgA is present at a concentration of 5 milligrams per dose.

6. The method of claim 3 wherein the IgA is conjugated to the recombinant J chain by a disulfide linkage.

7. The method of claim 3 further comprising the step of adding a pharmaceutical excipient.

8. The method of claim 3 further comprising the step of adding a buffering agent.

9. The method of claim 3 wherein the IgA is conjugated to the recombinant secretory component by a disulfide linkage.

* * * * *